(12) United States Patent
Tian et al.

(10) Patent No.: US 11,084,775 B1
(45) Date of Patent: Aug. 10, 2021

(54) CINNAMYL ALCOHOL ACITRETIN ESTER WITH ANTIOXIDANT ACTIVITY AND A METHOD OF PREPARING THE SAME

(71) Applicants: Bin Tian, Xi'an (CN); Juan Li, Xi'an (CN); Gennian Mao, Xi'an (CN); Limei Wang, Xi'an (CN); Mudan Xu, Xi'an (CN); Xingke Ju, Xi'an (CN); Han Li, Xi'an (CN); Yanjun Li, Xi'an (CN); Qiao Zeng, Xi'an (CN); Chengyuan Liang, Xi'an (CN)

(72) Inventors: Bin Tian, Xi'an (CN); Juan Li, Xi'an (CN); Gennian Mao, Xi'an (CN); Limei Wang, Xi'an (CN); Mudan Xu, Xi'an (CN); Xingke Ju, Xi'an (CN); Han Li, Xi'an (CN); Yanjun Li, Xi'an (CN); Qiao Zeng, Xi'an (CN); Chengyuan Liang, Xi'an (CN)

(73) Assignee: SHAANXI UNIVERSITY OF SCIENCE AND TECHNOLOGY, Xi'an (CN)

(*) Notice: Subject to any disclaimer, the term of this patent is extended or adjusted under 35 U.S.C. 154(b) by 0 days.

(21) Appl. No.: 16/996,519

(22) Filed: Aug. 18, 2020

(51) Int. Cl.
*C07C 69/618* (2006.01)
*C07C 67/52* (2006.01)
*C07C 67/08* (2006.01)

(52) U.S. Cl.
CPC ............ *C07C 69/618* (2013.01); *C07C 67/08* (2013.01); *C07C 67/52* (2013.01)

(58) Field of Classification Search
None
See application file for complete search history.

(56) References Cited

U.S. PATENT DOCUMENTS 10,836,703 B1 * 11/2020 Wang ...................... C07C 69/52

* cited by examiner

*Primary Examiner* — Amy C Bonaparte
(74) *Attorney, Agent, or Firm* — SZDC Law P.C.

(57) ABSTRACT

A compound having the formula (I):

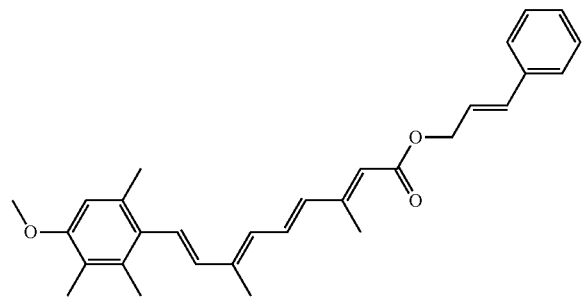

(I) is disclosed. A method of preparing the compound of formula (I) is also disclosed.

15 Claims, 1 Drawing Sheet

CINNAMYL ALCOHOL ACITRETIN ESTER WITH ANTIOXIDANT ACTIVITY AND A METHOD OF PREPARING THE SAME

FIELD OF THE INVENTION

The present invention relates to a food chemistry area, more specifically, to a cinnamyl alcohol acitretin ester having antioxidant activity and a method of preparing the same.

BACKGROUND OF THE INVENTION

Lipid oxidation is one of the chemical reasons for the deterioration of food quality, especially foods rich in unsaturated fatty acids are prone to oxidation to generate peroxide lipids. As a result, rancidity and toxicity appear through oxidative decomposition and rearrangement reactions, and the food loses its edible value. Therefore, compounds with antioxidant activity have attracted much attention.

The main chemical components of cinnamon are volatile oil, polysaccharides, polyphenols, flavonoids and trace elements, etc. It has a variety of pharmacological effects such as dilation of blood vessels, anti-gastric ulcer, antibacterial and anti-oxidation. Cinnamon, as a traditional Chinese medicinal material for both medicine and food, is clinically mainly used in the treatment of cardiovascular diseases and gastrointestinal diseases. In addition, the deep processing application of cinnamon is mainly concentrated in the fields of food preservatives and spices, daily chemical products, functional material products, etc.; cinnamaldehyde can also be used as an intermediate to synthesize benzaldehyde, cinnamyl alcohol (compound of formula (II)), cinnamic acid, benzoic acid and other derivatives. It is further applied to many fields such as flavor, medicine, pesticide and so on.

Acitretin (compound of formula (III)) is a synthetic analogue of aromatic vitamin A, which is the active metabolite of etretinate, and is used to treat severe psoriasis, keratinization diseases and other skin diseases.

In the present invention, cinnamyl alcohol is modified by the acitretin structure to obtain a cinnamyl alcohol acitretin ester. The ester compound has excellent antioxidant activity and high medical research and application value in the field of antioxidant health products.

SUMMARY OF THE INVENTION

In one embodiment, the present application provides a cinnamyl alcohol acitretin ester has the following formula (I):

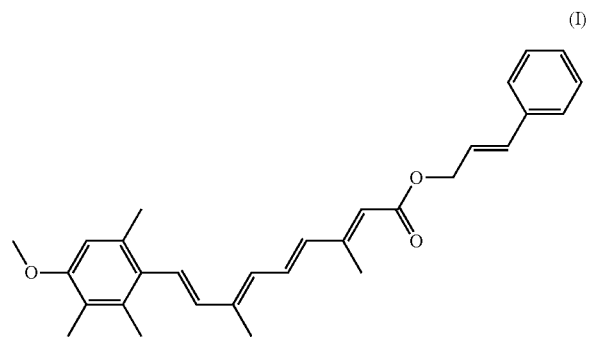

In another embodiment, a method of preparing the compound of formula (I) includes reacting the compound of formula (II) with the compound of formula (III) in organic solvent to obtain the compound of formula (I):

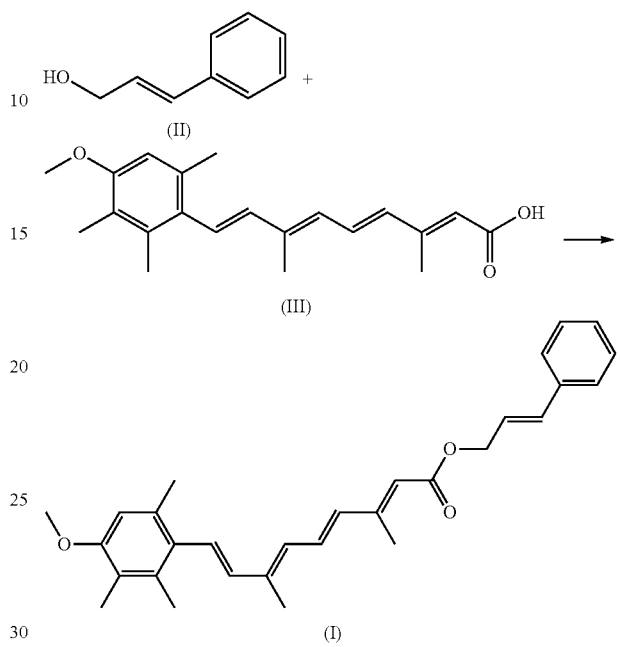

In another embodiment, the reaction of the compound of formula (II) with the compound of formula (III) includes the following steps: placing the compound of formula (II) and the compound of formula (III), in a molar ratio of 1:1 to 1:1.3, in a reactor; adding an organic solvent and a catalytic amount of EDC to obtain a reaction mixture; and heating the reaction mixture at 50-80° C. for 5-10 hours; and purifying the crude product on a silica gel fresh chromatography column with petroleum ether and ethyl acetate as an eluent to obtain the compound of formula (I).

In another embodiment, the organic solvent is toluene, tetrahydrofuran or acetonitrile.

In another embodiment, the organic solvent is acetonitrile.

In another embodiment, the molar ratio of the compound of formula (II) and the compound of formula (III) is 1:1.1.

In another embodiment, the reaction mixture is heated at 70° C.

In another embodiment, the reaction mixture is heated for 8 hours.

In another embodiment, the eluent is petroleum ether: ethyl acetate=3:10 (v/v).

In another embodiment, the reaction of the compound of formula (II) with the compound of formula (III) comprises the following steps: placing the compound of formula (II), a catalyst, and an ionic liquid in a reactor under nitrogen atmosphere, the catalyst being 12-molybdosilicic acid hydrate ($H_6Mo_{12}O_{41}Si$); adding the compound of formula (III) to the reactor to form a reaction mixture; heating the reaction mixture at 25-50° C. for 6-12 hours; placing the reaction mixture in a separating funnel to separate a crude product; purifying the crude product by recrystallization in methanol to obtain the compound of formula (I); and recycling the ionic liquid.

In another embodiment, the ionic liquid is 1-butyl-3-methylimidazolium tetrafluoroborate ([BMIM][$BF_4$]).

In another embodiment, the molar ratio of the compound of formula (II) and the compound of formula (III) is 1:1.1.

In another embodiment, the reaction mixture is heated at 25° C.

In another embodiment, the reaction mixture is heated for 10 hours.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

In the drawings.

DETAILED DESCRIPTION OF THE ILLUSTRATED EMBODIMENTS

Figure 1:
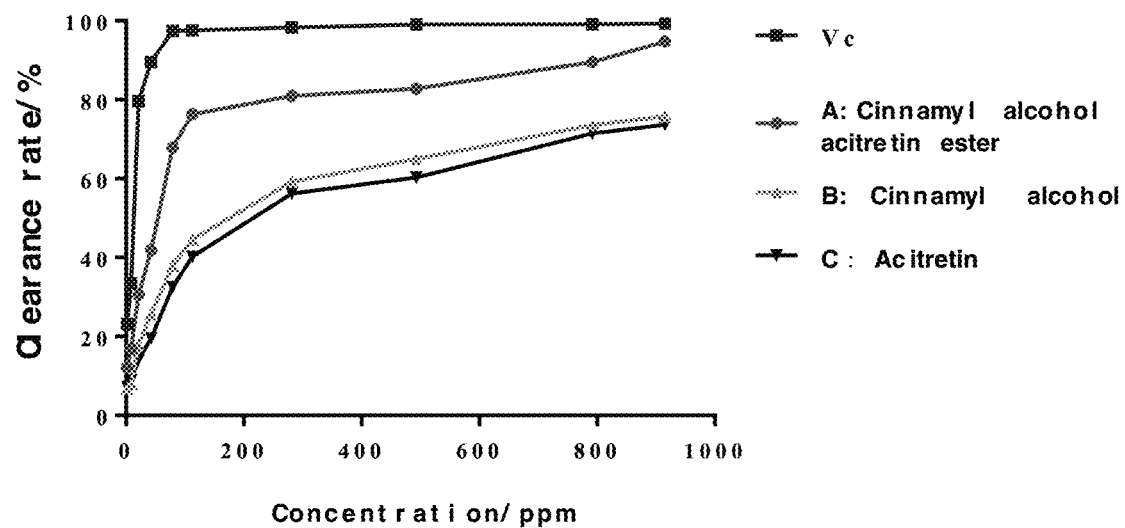
FIG. 1 shows the scavenging rate of the cinnamyl alcohol acitretin ester and control solution on DPPH free radicals.

Reference will now be made in detail to embodiments of the present invention, example of which is illustrated in the accompanying drawings. The following examples illustrate the present invention, but the present invention is not limited to the following examples.

Example 1

Preparation of compound of formula (I) ((2E,4E, 6E,8E)-cinnamyl 9-(4-methoxy-2,3, 6-trimethylphenyl)-3,7-dimethylnona-2,4, 6,8-tetraenoate)

In a 250 mL three-necked flask, 67.0 mg (0.50 mmol) of cinnamyl alcohol and 95.7 mg (0.50 mmol) EDC (1-ethyl-3-(3 dimethylaminopropyl)carbodiimide) were dissolved in 60 mL of acetonitrile under nitrogen atmosphere. 179.4 mg (0.55 mmol) of acitretin was dissolved in 60 mL of acetonitrile, and added dropwise to the reaction mixture by a separatory funnel. After the completion of the dropwise addition, the temperature was raised to 70° C., and the reaction was carried out for 8 hours. Thin layer chromatography was used to track the reaction to completion, heating was stopped, and the protective device was removed. The concentrated solution was washed in water, extracted with ethyl acetate, dried and concentrated to obtain a crude product. The crude product was further purified by silica gel column chromatography, with petroleum ether:ethyl acetate=3:10 as eluent, and the eluent was concentrated under reduced pressure and dried to obtain 164.9 mg of the title compound, a yield of 74.56%.

$^1$H-NMR (400 MHz, DMSO-$d_6$) δ (ppm): 7.43 (3H, d), 7.35 (2H, d), 6.60 (3H, s), 6.45 (3H, s), 6.29 (2H, s), 5.81 (1H, s) 4.16 (2H, s), 3.78 (3H, s), 3.32 (3H, s), 2.26 (9H, s), 2.11 (3H, s); $^{13}$C-NMR (400 MHz, DMSO-$d_6$) δ (ppm): 168.2, 156.1, 152.0, 131.3, 130.9, 129.0, 128.6, 126.6, 120.1, 110.6, 61.9, 55.8, 21.6, 17.6, 13.9, 13.1, 12.2.

Example 2

Preparation of Compound of Formula (I)

In a 250 mL three-necked flask, 67.0 mg (0.50 mmol) of cinnamyl alcohol and 95.7 mg (0.50 mmol) EDC were dissolved in 60 mL of toluene under nitrogen atmosphere. 179.4 mg (0.55 mmol) of acitretin was dissolved in 60 mL of toluene, and added dropwise to the reaction mixture by a separatory funnel. After the completion of the dropwise addition, the temperature was raised to 80° C., and the reaction was carried out for 5 hours. Thin layer chromatography was used to track the reaction to completion, heating was stopped, and the protective device was removed. The concentrated solution was washed in water, extracted with ethyl acetate, dried and concentrated to obtain a crude product. The crude product was further purified by silica gel column chromatography, with petroleum ether:ethyl acetate=3:10 as eluent, and the eluent was concentrated under reduced pressure and dried to obtain 162.4 mg of the title compound, a yield of 73.45%.

Example 3

Preparation of Compound of Formula (I)

In a 250 mL three-necked flask, 67.0 mg (0.50 mmol) of cinnamyl alcohol and 95.7 mg (0.50 mmol) EDC were dissolved in 60 mL of tetrahydrofuran under nitrogen atmosphere. 195.7 mg (0.60 mmol) of acitretin was dissolved in 60 mL of tetrahydrofuran, and added dropwise to the reaction mixture by a separatory funnel. After the completion of the dropwise addition, the temperature was raised to 60° C., and the reaction was carried out for 7 hours. Thin layer chromatography was used to track the reaction to completion, heating was stopped, and the protective device was removed. The concentrated solution was washed in water, extracted with ethyl acetate, dried and concentrated to obtain a crude product. The crude product was further purified by silica gel column chromatography, with petroleum ether: ethyl acetate=3:10 as eluent, and the eluent was concentrated under reduced pressure and dried to obtain 145.4 mg of the title compound, a yield of 65.77%.

Example 4

Preparation of Compound of Formula (I)

In a 250 mL three-necked flask, 67.0 mg (0.50 mmol) of cinnamyl alcohol and 95.7 mg (0.50 mmol) EDC were dissolved in 60 mL of toluene under nitrogen atmosphere. 179.4 mg (0.55 mmol) of acitretin was dissolved in 60 mL of toluene, and added dropwise to the reaction mixture by a separatory funnel. After the completion of the dropwise addition, the temperature was raised to 60° C., and the reaction was carried out for 7 hours. Thin layer chromatography was used to track the reaction to completion, heating was stopped, and the protective device was removed. The concentrated solution was washed in water, extracted with ethyl acetate, dried and concentrated to obtain a crude product. The crude product was further purified by silica gel column chromatography, with petroleum ether:ethyl acetate=3:10 as eluent, and the eluent was concentrated under reduced pressure and dried to obtain 148.9 mg of the title compound, a yield of 67.35%.

Example 5

Preparation of Compound of Formula (I)

In a 250 mL three-necked flask, 67.0 mg (0.50 mmol) of cinnamyl alcohol and 95.7 mg (0.50 mmol) EDC were dissolved in 60 mL of acetonitrile under nitrogen atmosphere. 179.4 mg (0.55 mmol) of acitretin was dissolved in 60 mL of acetonitrile, and added dropwise to the reaction mixture by a separatory funnel. After the completion of the dropwise addition, the temperature was raised to 60° C., and the reaction was carried out for 8 hours. Thin layer chromatography was used to track the reaction to completion, heating was stopped, and the protective device was removed. The concentrated solution was washed in water, extracted with ethyl acetate, dried and concentrated to obtain a crude product. The crude product was further purified by silica gel column chromatography, with petroleum ether: ethyl acetate=3:10 as eluent, and the eluent was concentrated under reduced pressure and dried to obtain 149.3 mg of the title compound, a yield of 67.53%.

Example 6

Preparation of Compound of Formula (I)

In a 250 mL three-necked flask, 67.0 mg (0.50 mmol) of cinnamyl alcohol and 95.7 mg (0.50 mmol) EDC were dissolved in 60 mL of tetrahydrofuran under nitrogen atmosphere. 179.4 mg (0.55 mmol) of acitretin was dissolved in 60 mL of tetrahydrofuran, and added dropwise to the reaction mixture by a separatory funnel. After the completion of the dropwise addition, the temperature was raised to 65° C., and the reaction was carried out for 10 hours. Thin layer chromatography was used to track the reaction to completion, heating was stopped, and the protective device was removed. The concentrated solution was washed in water, extracted with ethyl acetate, dried and concentrated to obtain a crude product. The crude product was further purified by silica gel column chromatography, with petroleum ether: ethyl acetate=3:10 as eluent, and the eluent was concentrated under reduced pressure and dried to obtain 147.2 mg of the title compound, a yield of 66.57%.

Example 7

Preparation of Compound of Formula (I)

In a 250 mL three-necked flask, 67.0 mg (0.50 mmol) of cinnamyl alcohol, 179.4 mg (0.55 mmol) of acitretin and 8.3 mg (0.005 mmol) silicomolybdic acid were dissolved in 100 mL of 1-butyl-3-methylimidazolium tetrafluoroborate under nitrogen atmosphere. After full dissolution, the temperature was raised to 25° C. and the reaction was carried out for 10 hours. Thin layer chromatography was used to track the reaction to completion, heating was stopped, and the protective device was removed. The reaction mixture was allowed to separate into layers to give a crude product. The crude product was recrystallized with 70 mL methanol and dried to obtain 187.8 mg of the title compound, a yield of 84.95%. 1-Butyl-3-methylimidazolium tetrafluoroborate was recovered for reuse.

Example 8

Preparation of Compound of Formula (I)

In a 250 mL three-necked flask, 67.0 mg (0.50 mmol) of cinnamyl alcohol, 179.4 mg (0.55 mmol) of acitretin and 8.3 mg (0.005 mmol) silicomolybdic acid were dissolved in 100 mL of 1-butyl-3-methylimidazolium tetrafluoroborate under nitrogen atmosphere. After full dissolution, the temperature was raised to 50° C. and the reaction was carried out for 6 hours. Thin layer chromatography was used to track the reaction to completion, heating was stopped, and the protective device was removed. The reaction mixture was allowed to separate into layers to give a crude product. The crude product was recrystallized with 70 mL methanol and dried to obtain 179.7 mg of the title compound, a yield of 81.28%. 1-Butyl-3-methylimidazolium tetrafluoroborate was recovered for reuse.

Example 9

The antioxidant activity of the cinnamyl alcohol acitretin ester measured by a DPPH radical scavenging activity assay 2,2-Diphenyl-1-picryl hydrazyl (DPPH) is an organic compound composed of a stable organic radical. In the DPPH molecule, due to the presence of multiple electron-withdrawing $—NO_2$ and large $\pi$ bonds of the benzene ring, nitrogen free radical is stabilized. Its methanol solution is purple and has a maximum absorption peak at 517 nm. After the addition of an antioxidant, DPPH captures an electron to be paired with the free electron, and the purple fades and turns into a yellow substance. The absorption at 517 nm disappears, and the degree of fading is quantitatively related to the number of electrons it captures. Based on this principle, a spectrophotometer is used to detect the change of the absorbance of the DPPH radical and the sample solution, and the ability of the sample to provide hydrogen atoms and scavenge free radicals can be measured.

Preparation of DPPH Solution

Measuring exact amount of 2,2-diphenyl-1-picryl hydrazyl (DPPH) and dissolving in toluene to prepare a 0.2 mmoL/L DPPH solution; being stored at 0° C. in dark.

Preparation of Test Solutions

Vc (vitamin C, positive control), cinnamyl alcohol acitretin ester (sample), cinnamyl alcohol (control) and acitretin (control). The test solutions were subjected to gradient dilution with toluene, and three sets of controls were separately dissolved in a test tube with a certain amount of toluene to prepare the same concentration gradient as the sample. The corresponding three groups of control solutions were obtained (gradient settings are shown in Table 1).

TABLE 1

| Dilution gradient of the test solution | | |
| --- | --- | --- |
| Number | Test solution | Concentration gradient/ppm |
| Vc | Vc | 1.76, 8.80, 21.12, 42.24, 79.20, 112.64, 281.60, 492.80, 792.00, 915.20 |
| A | Cinnamyl alcohol acitretin ester | 1.76, 8.80, 21.12, 42.24, 79.20, 112.64, 281.60, 492.80, 792.00, 915.20 |
| B | Cinnamyl alcohol | 1.76, 8.80, 21.12, 42.24, 79.20, 112.64, 281.60, 492.80, 792.00, 915.20 |
| C | Acitretin | 1.76, 8.80, 21.12, 42.24, 79.20, 112.64, 281.60, 492.80, 792.00, 915.20 |

Measurements:

Solution liquid absorbance measurement: Take 2 mL of sample solution (Table 1: Vc, B,C), adding 2 mL of DPPH solution with concentration of $2 \times 10^{-4}$ moL/L, mixing and reacting in the dark at room temperature for 30 min, adjusting to zero with toluene, and measuring at 517 nm. The absorbance Ai was simultaneously measured for the absorbance Aj of 2 mL of toluene mixed with 2 mL of the sample solution and the absorbance $A_0$ of 2 mL of DPPH solution mixed with 2 mL of toluene (The experimental results are shown in Table 2).

water; 20 mmol/L salicylic acid: 0.2765 g salicylic acid in a 100 mL volumetric flask, fix the volume to the scale with ethanol.

TABLE 2

Absorbance test results of each test solution

| Sample | Absorbance | Concentration/ppm | | | | | | | | |
|---|---|---|---|---|---|---|---|---|---|---|
| | | 1.76 | 8.80 | 21.12 | 42.24 | 79.20 | 112.64 | 281.60 | 492.80 | 792.00 | 915.20 |
| Vc | Ai | 0.718 | 0.624 | 0.222 | 0.142 | 0.091 | 0.078 | 0.076 | 0.070 | 0.074 | 0.065 |
| | Aj | 0.068 | 0.061 | 0.050 | 0.054 | 0.069 | 0.057 | 0.062 | 0.062 | 0.066 | 0.059 |
| | Ao | | | | | | 0.846 | | | | |
| A | Ai | 0.840 | 0.802 | 0.673 | 0.574 | 0.345 | 0.264 | 0.226 | 0.205 | 0.147 | 0.096 |
| | Aj | 0.047 | 0.052 | 0.046 | 0.049 | 0.055 | 0.050 | 0.054 | 0.049 | 0.053 | 0.048 |
| | Ao | | | | | | 0.903 | | | | |
| B | Ai | 0.881 | 0.870 | 0.773 | 0.709 | 0.614 | 0.550 | 0.409 | 0.360 | 0.270 | 0.255 |
| | Aj | 0.049 | 0.048 | 0.039 | 0.045 | 0.059 | 0.054 | 0.045 | 0.047 | 0.034 | 0.039 |
| | Ao | | | | | | 0.894 | | | | |
| C | Ai | 0.851 | 0.830 | 0.788 | 0.737 | 0.631 | 0.562 | 0.423 | 0.384 | 0.281 | 0.266 |
| | Aj | 0.051 | 0.045 | 0.049 | 0.043 | 0.050 | 0.047 | 0.046 | 0.041 | 0.035 | 0.039 |
| | Ao | | | | | | 0.862 | | | | |

Clearance rate is calculated in accordance with the following equation:

Clearance rate (%)=[1−(Ai−Aj)/$A_0$]*100%

Calculated clearance rate is shown in FIG. 1 and Table 3.

TABLE 3

DPPH clearance rate experiment results

| Concentration/ppm | Clearance rate/% ( n = 3) | | | |
|---|---|---|---|---|
| | Vc | A | B | C |
| 1.76 | 23.16 | 12.23 | 6.89 | 7.21 |
| 8.80 | 33.47 | 16.89 | 7.95 | 8.90 |
| 21.12 | 79.63 | 30.52 | 17.86 | 14.23 |
| 42.24 | 89.55 | 41.85 | 25.71 | 19.53 |
| 79.20 | 97.42 | 67.89 | 37.96 | 32.55 |
| 112.64 | 97.53 | 76.32 | 44.56 | 40.23 |
| 281.60 | 98.29 | 80.96 | 59.23 | 56.21 |
| 492.80 | 99.06 | 82.77 | 64.94 | 60.25 |
| 792.00 | 99.10 | 89.56 | 73.54 | 71.42 |
| 915.20 | 99.28 | 94.73 | 75.82 | 73.65 |

Example 10

The antioxidant activity of the cinnamyl alcohol acitretin ester measured by hydroxyl radical scavenging experiment Hydroxyl radical scavenging experiments use Fenton reaction to generate hydroxyl radicals, and salicylic acid reacts with the generated hydroxyl radicals to generate 2,3-dihydroxybenzoic acid. This substance has absorption at 510 nm. When antioxidants are added to the reaction system, it can reduce the production of hydroxyl radicals, thereby reducing the production of 2,3-dihydroxybenzoic acid. The color development of $H_2O_2$ is quantitatively related to the total antioxidant capacity of antioxidants. By using the fixed time reaction method, the absorbance of the reaction solution containing the tested substance was measured at 510 nm and compared with the blank solution, so as to determine the scavenging effect of the tested substance on hydroxyl radical.

Reagent Preparation:

1.5 mmol/L $FeSO_4$: 0.0417 g $FeSO_4$ in a 100 mL volumetric flask, adjusting the volume to the scale with distilled water; 6 mmol/L $H_2O_2$: 61 μL 30% $H_2O_2$ in a 100 mL volumetric flask, fix the volume to the scale with distilled Preparation of Sample Solution The cinnamyl alcohol acitretin ester synthesized in this experiment was diluted with acetonitrile according to the concentration gradient of 0.04, 0.07, 0.21, 0.35, 1.06, 1.76, 5.28, 8.80 (mg/mL) to prepare the sample solution to be tested. In the same way, the control samples (vitamin C, cinnamyl alcohol, acitretin) were diluted with the same concentration gradient with methanol to obtain the corresponding 3 groups of reference solution solutions. Gradient settings are shown in Table 4.

TABLE 4

Dilution gradient of the test solution

| Number | Test solution | Concentration gradient/(mg/mL) |
|---|---|---|
| Vc | Vc | 0.04, 0.07, 0.21, 0.35, 1.06, 1.76, 5.28, 8.80 |
| A | Cinnamyl alcohol acitretin ester | 0.04, 0.07, 0.21, 0.35, 1.06, 1.76, 5.28, 8.80 |
| B | Cinnamyl alcohol | 0.04, 0.07, 0.21, 0.35, 1.06, 1.76, 5.28, 8.80 |
| C | Acitretin | 0.04, 0.07, 0.21, 0.35, 1.06, 1.76, 5.28, 8.80 |

Measurements:

Taking 1 mL of the sample to be tested, adding 2 mL $FeSO_4$ solution with a concentration of 1.5 mmol/L and 0.6 mL salicylic acid with a concentration of 20 mmol/L, and finally adding 1.4 mL of $H_2O_2$ solution with a concentration of 6 mmol/L; reacting in a water bath for 30 minutes, and adjusting to zero with absolute ethanol; measuring the absorbance $A_i$ at 510 nm, measure the absorbance $A_j$ of 1.4 mL distilled water instead of $H_2O_2$ and the absorbance $A_0$ of 1 mL distilled water instead of the sample. The experimental results are shown in Table 5.

TABLE 5

Absorbance test results of each test solution

| Sample | Absorbance | Concentration/ppm | | | | | | | |
| --- | --- | --- | --- | --- | --- | --- | --- | --- | --- |
| | | 0.04 | 0.07 | 0.21 | 0.35 | 1.06 | 1.76 | 5.28 | 8.80 |
| Vc | Ai | 0.822 | 0.723 | 0.450 | 0.183 | 0.115 | 0.132 | 0.134 | 0.129 |
| | Aj | 0.041 | 0.047 | 0.051 | 0.065 | 0.079 | 0.101 | 0.115 | 0.120 |
| | Ao | 1.125 | | | | | | | |
| A | Ai | 0.940 | 0.799 | 0.758 | 0.659 | 0.598 | 0.551 | 0.490 | 0.397 |
| | Aj | 0.037 | 0.045 | 0.055 | 0.068 | 0.071 | 0.088 | 0.105 | 0.114 |
| | Ao | 1.197 | | | | | | | |
| B | Ai | 1.049 | 1.016 | 1.010 | 0.965 | 0.916 | 0.859 | 0.778 | 0.599 |
| | Aj | 0.032 | 0.034 | 0.057 | 0.069 | 0.080 | 0.093 | 0.126 | 0.165 |
| | Ao | 1.078 | | | | | | | |
| C | Ai | 1.053 | 1.043 | 0.992 | 0.946 | 0.892 | 0.854 | 0.776 | 0.636 |
| | Aj | 0.028 | 0.033 | 0.037 | 0.041 | 0.053 | 0.066 | 0.079 | 0.105 |
| | Ao | 1.059 | | | | | | | |

Clearance rate is calculated in accordance with the following equation:

$$\text{Clearance rate (\%)} = [1-(A_i-A_j)/A_o]*100\%$$

Figure 2:
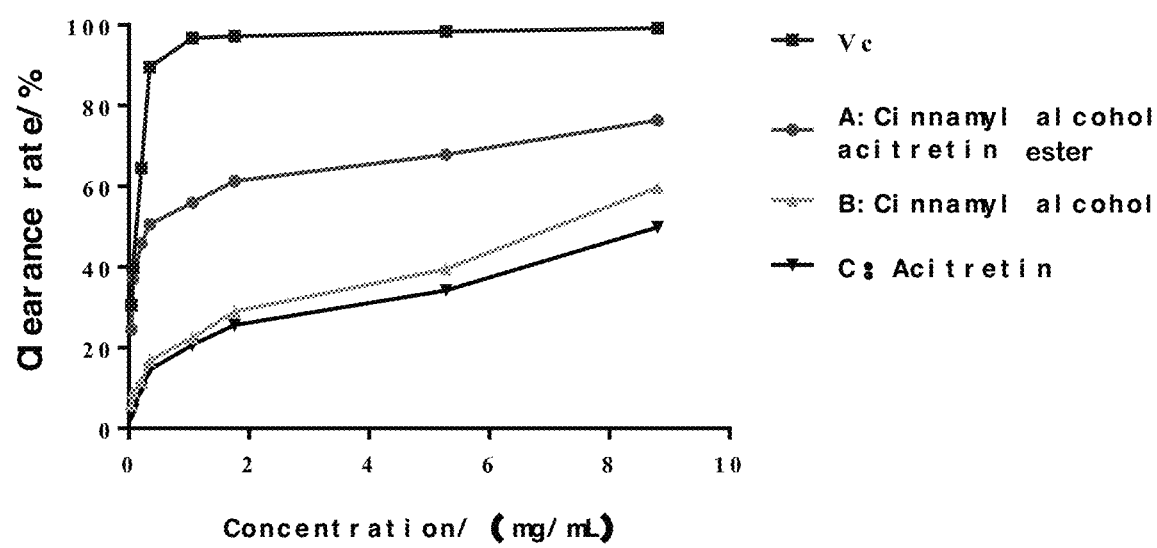
FIG. 2 shows the scavenging rate of the cinnamyl alcohol acitretin ester and the control solution on hydroxyl radicals.

Calculated clearance rate is shown in FIG. 2 and Table 6.

TABLE 6

DPPH clearance rate experiment results

| Concentration/ppm | Clearance rate/% ( n = 3) | | | |
| --- | --- | --- | --- | --- |
| | Vc | A | B | C |
| 0.04 | 30.55 | 24.55 | 5.69 | 3.21 |
| 0.07 | 39.85 | 36.93 | 8.95 | 4.65 |
| 0.21 | 64.51 | 45.85 | 11.52 | 9.78 |
| 0.35 | 89.55 | 50.63 | 16.86 | 14.55 |
| 1.06 | 96.77 | 55.96 | 22.45 | 20.74 |
| 1.76 | 97.21 | 61.32 | 28.95 | 25.63 |
| 5.28 | 98.35 | 67.85 | 39.52 | 34.19 |
| 8.80 | 99.18 | 76.39 | 59.74 | 49.86 |

As shown FIGS. 1-2 and Table 1-6, the antioxidant activity of the cinnamyl alcohol acitretin ester (A) was concentration-dependent, and the scavenging activity of the cinnamyl alcohol acitretin ester to DPPH radical and hydroxyl radical increased with the increase of concentration. In the concentration range, the highest scavenging rate of DPPH free radical was 94.73%, and the highest scavenging rate of hydroxyl radical was 76.39%. The hydroxytyrosol acitretin ester has similar scavenging ability to the positive control Vc group. Compared with the control group treated only with cinnamyl alcohol (B) and acitretin (C), the cinnamyl alcohol acitretin ester had the strongest scavenging ability to free radicals at the same concentration. The antioxidant activity at high concentration was much higher than that of cinnamyl alcohol (B) control group and acitretin (C) control group. The above experimental results show that the compound has excellent antioxidant activity and has a good application prospect.

What is claimed is:
1. A compound having the following formula (I):

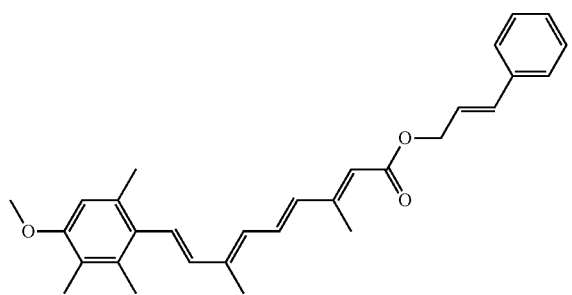 [SMILES: COc1cc(C)c(/C=C/C(C)=C/C=C/C(C)=C/C(=O)OC/C=C/c2ccccc2)c(C)c1C]

(I)

2. A method of preparing the compound of formula (I) of claim 1, comprising: reacting a compound of formula (II) with a compound of formula (III) to obtain the compound of formula (I):

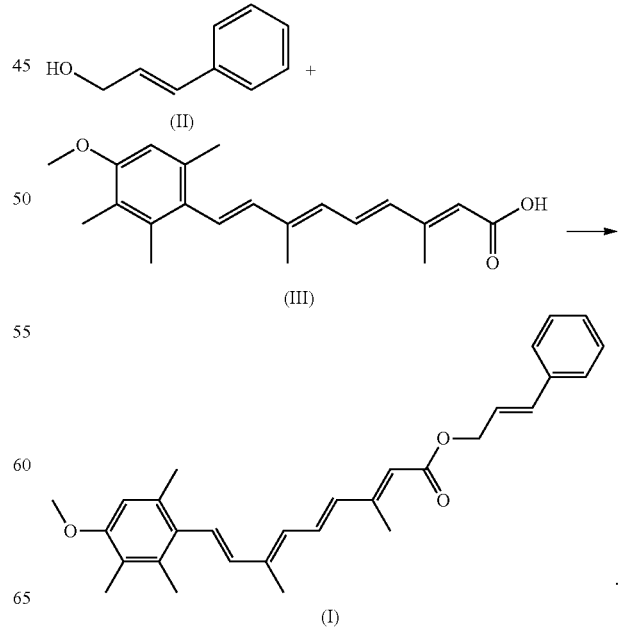

3. The method of claim 2, wherein the reaction of the compound of formula (II) with the compound of formula (III) comprises the following steps:
  placing the compound of formula (II) and the compound of formula (III), in a molar ratio of 1:1 to 1:1.3, in a reactor;
  adding an organic solvent and a catalytic amount of EDC under nitrogen atmosphere to obtain a reaction mixture; and
  heating the reaction mixture at 50-80° C. for 5-10 hours; and
  purifying the crude product on a silica gel fresh chromatography column with petroleum ether and ethyl acetate as an eluent to obtain the compound of formula (I).

4. The method of claim 3, wherein the organic solvent is toluene, tetrahydrofuran or acetonitrile.

5. The method of claim 4, wherein the organic solvent is acetonitrile.

6. The method of claim 3, wherein the molar ratio of the compound of formula (II) and the compound of formula (III) is 1:1.1.

7. The method of claim 3, wherein the reaction mixture is heated at 70° C.

8. The method of claim 3, wherein the reaction mixture is heated for 8 hours.

9. The method of claim 3, wherein the eluent is petroleum ether:ethyl acetate=3:10 (v/v).

10. The method of claim 2, wherein the reaction of the compound of formula (II) with the compound of formula (III) comprises the following steps:
  placing the compound of formula (II), a catalyst, and an ionic liquid in a reactor under nitrogen atmosphere, the catalyst being 12-molybdosilicic acid hydrate ($H_6Mo_{12}O_{41}Si$);
  adding the compound of formula (III) to the reactor to form a reaction mixture;
  heating the reaction mixture at 25-50° C. for 6-12 hours;
  placing the reaction mixture in a separating funnel to separate a crude product;
  purifying the crude product by recrystallization in methanol to obtain the compound of formula (I); and
  recycling the ionic liquid.

11. The method of claim 10, wherein the ionic liquid is 1-butyl-3-methylimidazolium tetrafluoroborate ([BMIM][$BF_4$]).

12. The method of claim 10, wherein the compound of formula (II) and the compound (III) have a molar ratio of 1:1 to 1:1.3.

13. The method of claim 12, wherein the molar ratio of the compound of formula (II) and the compound of formula (III) is 1:1.1.

14. The method of claim 10, wherein the reaction mixture is heated at 25° C.

15. The method of claim 10, wherein the reaction mixture is heated for 10 hours.

* * * * *